United States Patent [19]

Knoll et al.

[11] Patent Number: 4,904,669
[45] Date of Patent: Feb. 27, 1990

[54] THIAZOLO/4,5-C/QUINOLINES AS MAJOR TRANQUILIZERS

[75] Inventors: József Knoll; Edit Berényi née Poldermann; Katain Budainée Simonyi; Berta Knoll; Zsuzsa Fürts; Julia Timár; Gabriella Zsila; Ildikó Niklya; Lujza Petocz; Attila Mándi, all of Budapest, Hungary

[73] Assignee: EGIS Gyogyszergyar, Budapest, Hungary

[21] Appl. No.: 929,353

[22] Filed: Nov. 12, 1986

[30] Foreign Application Priority Data

Nov. 12, 1985 [HU] Hungary .............. 4304/85

[51] Int. Cl.⁴ .................. A61K 31/47; C07D 513/04
[52] U.S. Cl. ............................ 514/293; 546/83
[58] Field of Search .................. 546/83; 514/293

[56] References Cited

PUBLICATIONS

Bachman, B., et al., *J. Am. Chem. Soc.*, 69, 365 (1947).

*Primary Examiner*—Richard A. Schwartz
*Attorney, Agent, or Firm*—Keil & Weinkauf

[57] ABSTRACT

The invention relates to new thiazolo[4,5-c]quinoline derivatives of the general Formula I

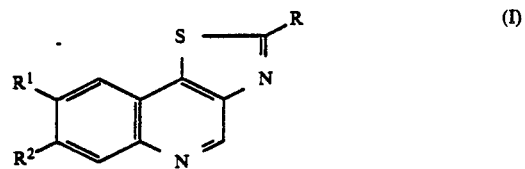

and acid addition salts thereof, a process for the preparation of the same and pharmaceutical compositions comprising the said compounds.

The substituent definition of the general Formula I is as follows:
R stands for hydrogen; a straight or branched chained alkyl group having 2-5 carbon atoms optionally substituted by one or more halogen atom(s); phenyl or phenyl-(lower alkyl) optionally bearing one or more substituent(s) on the phenyl ring;
$R^1$ and $R^2$ are identical or different and stand for hydrogen, halogen or lower alkyl).

The compounds of the general Formula I possess valuable central nervous depressive properties.

9 Claims, No Drawings

THIAZOLO/4,5-C/QUINOLINES AS MAJOR TRANQUILIZERS

This invention relates to new thiazolo[4,5-c]-isoquinoline derivatives, a process for the preparation thereof and pharmaceutical compositions comprising the same.

Bachmann et al. [J. Am. Chem. Soc. 69, 365-371 (1947)] described 2-methyl-thiazolo[4,5-c]quinoline. The authors were, however, completely silent in disclosing any biological activity of the said compound.

According to an aspect of the present invention there are provided new thiazolo[4,5-c]quinoline derivatives of the general Formula I

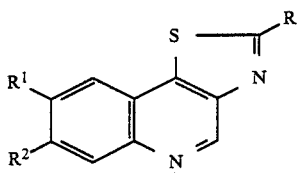

(wherein
R stands for hydrogen; a straight or branched chained alkyl group having 2-5 carbon atoms optionally substituted by one or more halogen atom(s); or phenyl or phenyl-(lower alkyl) optionally bearing one or more substituent(s) on the phenyl ring;
$R^1$ and $R^2$ are identical or different and stand for hydrogen, halogen or lower alkyl),
and acid addition salts thereof.

The term "straight or branched chain alkyl group having 2-5 carbon atoms" may be e.g. ethyl, n- or isopropyl, n-butyl, sec. butyl, isobutyl or tert. butyl, n-amyl or isoamyl. If R stands for phenyl or phenyl-(lower alkyl), the phenyl ring may optionally bear one or more identical or different substituent(s), e.g. halogen, lower alkyl, lower alkoxy, hydroxy, nitro, amino or mono- or dialkylamino etc. The phenyl-(lower alkyl) group may be e.g. benzyl or β-phenyl-ethyl. The term "lower" relates to straight or branched chain groups having 1-4 carbon atoms. The term "lower alkoxy" relates to straight or branched chain alkoxy groups having 1-4 carbon atoms (e.g. methoxy, ethoxy, n-propoxy or isopropoxy).

The "straight or branched chain alkyl group having 2-5 carbon atoms" (R) may be optionally substituted by one or more halogen atom(s), e.g. chloromethyl, dichloromethyl, trichloromethyl, trifluoromethyl, β-chloro-ethyl etc. The term "halogen" encompasses the fluorine, chlorine, bromine or iodine atom(s).

The acid addition salts of the compounds of the general Formula I may be formed with inorganic acids (e.g. mineral acids such as hydrochloric acid, hydrogen bromide, sulfuric acid, phosphoric acid etc.) or organic acids (e.g. malic acid, fumaric acid, tartaric acid, methane sulfonic acid, ethanesulfonic acid etc.). The pharmaceutically acceptable salts formed with pharmaceutically acceptable inorganic or organic acids are particularly preferred. As advantageous representatives of the pharmaceutically acceptable acid addition salts the hydrochlorides and ethanesulfonates may be mentioned.

A particularly preferred representative of the compounds of the general Formula I is the thiazolo[4,5-c]quinoline and pharmaceutically acceptable acid addition salts—particularly the hydrochloride and ethanesulfonate—thereof.

According to a further aspect of the present invention there is provided a process for the preparation of compounds of the general Formula I (wherein
R stands for hydrogen; a straight or branched chained alkyl group having 2-5 carbon atoms optionally substituted by one or more halogen atom(s); or phenyl or phenyl-(lower alkyl) optionally bearing one or more substituent(s) on the phenyl ring;
$R^1$ and $R^2$ are identical or different and stand for hydrogen, halogen or lower alkyl),
and pharmaceutically acceptable salts thereof, which comprises (a) reacting a 3-amino-4-mercapto-quinoline of the general Formula II

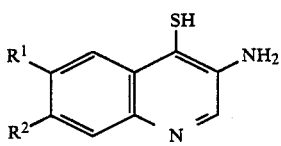

(wherein $R^1$ and $R^2$ are as stated above) or an acid addition salt thereof with a carboxylic acid of the general Formula III

R—COOH (III)

(wherein R is as stated above) or a reactive derivative thereof; or (b) reacting a 3-amino-4-mercapto-quinoline of the general Formula II or an acid addition salt thereof with an aldehyde of the general Formula V

R—CHO (V)

(wherein R is as stated above) in the presence of an oxidizing agent; or (c) cyclising a compound of the general Formula (IV)

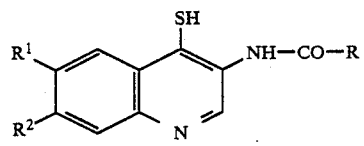

(wherein R, $R^1$ and $R^2$ are as stated above); and, if desired, converting a compound of the general Formula I thus obtained into an acid addition salt or setting free the same from a salt.

According to process a) a 3-amino-4-mercapto-quinoline of the general Formula II or an acid addition salt (e.g. hydrochloride) thereof is reacted with a carboxylic acid of the general Formula III or a reactive derivative thereof. As reactive acid derivative preferably an anhydride, a trialkyl ortho carboxylate, acid halide or ester may be used. The reactive derivative of the acid (e.g. anhydride or trialkyl ortho carboxylate) may be used in an excess when it serves as reaction medium, too. One may also proceed by using the compound of the Formula II and the acid of the general Formula III or a reactive derivative thereof in equimolar amounts and carrying out the reaction in the presence of an inert solvent. As reaction medium preferably aromatic hydrocarbons (e.g. benzene, toluene or xylene) may be used. The reaction may be accomplished at a temperature between 20° C. and 160° C.; one may preferably work at the boiling point of the reaction mixture.

According to a particularly preferred embodiment of process a) a 3-amino-4-mercapto-quinoline of the Formula II is reacted with an excess of a trialkyl ortho carboxylate at a temperature between 100° C. and 160° C., preferably at a temperature being by 5°–10° C. lower than the boiling point of the trialkyl ortho carboxylate and removing from the reaction mixture continuously the alkanol formed in the reaction. One may preferably use a triethyl ortho carboxylate. The reaction having been completed the reaction mixture is cooled to room temperature.

According to a further preferred embodiment the compound of the general Formula II is reacted in an excess of an anhydride of the acid of the general Formula III at the boiling point, but at a temperature below 160° C.

The compound of the Formula I may be isolated from the reaction mixture in the form of the free base or an acid addition salt thereof by known methods (e.g. extraction, cooling, evaporation or filtration).

According to process b) a 3-amino-4-mercapto-quinoline of the general Formula II or an acid addition salt thereof (preferably the hydrochloride) is reacted with an aldehyde of the general Formula V in the presence of a suitable oxidizing agent, preferably air. The reaction may be preferably accomplished in the presence of an inert organic solvent. As reaction medium advantageously an alkanol (e.g. methanol, ethanol or isopropanol) may be used. The reaction may be carried out at 20°–160° C., preferably at the boiling point of the reaction mixture. The aldehyde of the general Formula V may be used in equimolar amount or in a slight excess (5–20%).

The compound of the Formula I may be isolated from the reaction mixture by known methods (e.g. cooling, dilution with water, filtration).

According to process c) a 3-acylamido-4-mercapto-quinoline of the general Formula IV is subjected to cyclisation. Ring closure may be preferably carried out in an inert solvent. As reaction medium preferably an aromatic hydrocarbon (e.g. benzene, toluene or xylene) or a halogenated hydrocarbon (e.g. chlorobenzene) may be used. The reaction may be carried out at elevated temperature, particularly at 100°–180° C.

Cyclisation may be enhanced by carrying out the reaction in the presence of a dehydrating agent. Polyphosphoric acid proved to be particularly useful for this purpose. One may particularly advantageously proceed by carrying out the reaction in an excess of polyphosphoric acid as reaction medium under heating in the absence of an organic solvent.

The compound of the Formula I can be isolated from the reaction mixture by known methods (e.g. dilution with water, alkalization, extraction with an organic solvent).

The compound of the Formula I may be converted into a pharmaceutically acceptable acid addition salt by reacting with the corresponding acid. Salt formation may be accomplished in a manner known per se. The base of the Formula I can be set free from the acid addition salts by methods known per se.

The starting materials of the general Formulae II and IV are known and can be prepared as described in prior art [J. Am. Chem. Soc. 69, 365–371 (1947)].

The other starting materials (compounds of the general Formulae III and V are commercial products.

According to a further feature of the present invention there are provided pharmaceutical compositions comprising a thiazolo[4,5-c]quinoline of the general Formula I or a pharmaceutically acceptable acid addition salt thereof in admixture with suitable inert solid or liquid pharmaceutical carriers.

The pharmaceutical compositions may be suitable for oral (e.g. tablets, coated pills, dragées, hard or soft gelatine capsules, solutions, emulsions or suspensions), parenteral (e.g. injectable solutions) or rectal (e.g. suppositories) administration.

The pharmaceutical compositions of the present invention can be prepared by known methods of pharmaceutical industry by admixing a thiazolo[4,5-c]quinoline of the general Formula I or a pharmaceutically acceptable acid addition salt thereof with suitable inert solid or liquid pharmaceutical carriers and finishing the mixture in galenic form.

Tablets, coated pills, dragées and hard gelatine capsules may comprise as carrier e.g. lactose, maize starch, talc, magnesium carbonate, magnesium stearate, calcium carbonate, stearic acid or salts thereof etc. Soft gelatine capsules may comprise as carrier e.g. vegetable oils, fats, wax or polyols of suitable consistence. When preparing solutions or syrups, e.g. water, polyols, polyethylene glycol, saccharose or glucose may be used as carrier. Injectable solutions may comprise e.g. water, alcohols, polyols, glycerol or vegetable oils as carrier. Suppositories may comprise as carrier e.g. oils, wax, fats, cocoa butter or polyols of suitable consistence.

The pharmaceutical compositions of the present invention may also comprise conventional auxiliary agents generally used in pharmaceutical industry. From the broad scope of conventional additives the wetting, dispersing, conserving, emulsifying agents, solubilizers, colouring agents, sweeting agents, aroma substances and salts suitable for modifying the osmotic pressure can be mentioned.

The daily dosage of the thiazolo[4,5-c]quinoline may vary between wide ranges. Just of informative character it can be noticed that the dose of the compound of the general Formula I on oral administration may be between about 20 mg/kg and about 1000 mg/kg, while the parenteral dose may amount to from about 5 mg/kg to about 250 mg/kg. We wish to note that the above intervals are but of an approximate nature and the actual dose always depends on various factors (e.g. seriousness of the disease, age and condition of the patient etc.) and is determined by the physician. The actual dose may be below or above the said limits, too.

The compounds of the general Formula I and pharmaceutically acceptable acid addition salts thereof possess valuable highly interesting and special spectrum of effect. The compounds of the general Formula I exhibit a central nervous depressive effect being different from that of known central depressive agents. Contrary to major tranquillants, the compounds of the general Formula I do not inhibit non-specific activation mechanism and therefore, even if administered in high doses, enable the escape of animals in the one session unconditioned reflex test. Conventional tranquillants cause complete inhibition of the said reaction already in minimal doses.

The main difference of action between the compounds of the general Formula I and benzodiazepines resides in the fact that the compounds of the general Formula I are void of spasmolytic effect and simultaneously show a significantly stronger central depressive effect than benzodiazepines. Moreover, the compounds of the general Formula I are not bound to benzodiazepine receptors.

The pharmacological activity of the new compounds of the general Formula I is demonstrated by the following tests.

1. Toxicity Studies

Acute toxicity was assessed on CFY rats (100–160 g.). Groups of 10 rats were used. The compounds were administered orally (in volume of 10 ml/kg) and s.c. (in volume of 5 ml/kg). In the case of oral administration the animals starved for 16 h before the experiment. Each dose was administered to a group of animals equally subdivided into males and females. Deaths occurring within 48 h were considered. $LD_{50}$ values were calculated on the basis of the graphical method of Litchfield and Wilcoxon.

Thiazolo[4,5-c]quinoline-hydrochloride
$LD_{50}$ = 55 mg/kg i.v.
260 mg/kg s.c.
350 mg/kg p.o.
Thiazolo[4,5-c]quinoline-ethanesulfonate
$LD_{50}$ = 51 mg/kg i.v.
280 mg/kg s.c.
290 mg/kg p.o.

2. Hot Plate Test

The method of Woolfe and McDonald (1944) modified by Pórszász and Herr (1950) was used. The effect of each dose of the drugs was checked on a group of 10 rats. The experiments were performed on metal plates maintained at 56° C. The latency time of pain reactions was determined prior to and 1 h after the administration of the test compound. It was regarded as 100% effect if the reaction time was prolonged by more than 2.5 times the control value.

Thiazolo[4,5-c]quinoline-hydrochloride
$ED_{50}$ = 7.5 mg/kg s.c.
60 mg/kg p.o.
Thiazolo[4,5-c]quinoline-ethanesulfonate
$ED_{50}$ = 8 mg/kg s.c.
72 mg/kg p.o.

3. Algolytic Test

The experiments were performed according to a method described in detail earlier (Knoll 1967). The essence of the method is that the i.v. or s.c. administration of 10 mg/kg morphine produces complete analgesia in the rat so that laparatomy can be performed without the slightest sign of pain or straining or the appearance of postoperative prostration. Sensation of pain is expressed in arbitrary units on the basis of well defined criteria. Allotting 100 scores for pain reaction in untreated animals and 0 for complete analgesia, the $ED_{100}$ of a drug is the dose which blocks pain completely in the animal and $ED_{50}$ is the dose which reduces the number of scores to 50. Only narcotic analgesics are effective in this test. The test compounds do not influence the surgical pain sensation in the rat.

4. Writhing Test (Peritoneal)

The method originally described by van der Wende (1956) for rats modified by Witkin et al. (1961) and Koster and Anderson (1959), respectively, for mice was applied. Each dose was administered to a group of ten mice and after 20 min. 60 mg/kg of 0.6% acetic acid solution was injected i.p. As a result of chemical irritation of the peritoneum a characteristic writhing can be observed in 90% of control animals. Ten animals treated with compounds under test were kept under observation for 20 min. following i.p. injection of acid. The analgetic effect of individual doses was expressed in per cent:

$$\% \text{ analgetic effect} = 100 - \frac{\text{writhing treated}}{\text{writhing controls}} \times 100$$

The denominator was taken as 90% on the basis of preliminary control examination and the relevant literature.

If we compare the results observed in the hot plate tests, a weaker effectivity in the latter test could be seen. We can conclude therefore that in the hot plate test—which is non selective for the analgetic effect—not only the analgetic, but other, non specific central effects leading also to the prolongation of the reaction time has also been measured.

Thiazolo[4,5-c]quinoline-hydrochloride
$ED_{50}$ = 32 mg/kg s.c.
82 mg/kg p.o.
Thiazolo[4,5-c]quinoline-ethanesulfonate
$ED_{50}$ = 56 mg/kg s.c.
70 mg/kg p.o.

5. Narcosis Potentiating Effect

Sleeping times were determined on groups of ten male CFY rats weighing 150-200 g/s. Inactin (35 mg/kg) was injected into the tail vein. The times at which animals lost and regained their righting reflex were recorded. Control sleeping time: 425.49±34.2 s (n=120).

Both of the test substances significantly prolong the control barbiturate narcosis time:

thiazolo[4,5-c]quinoline-hydrochloride
$ED_{500}$ = 22 s.c.
22 p.o.
thiazolo[4,5-c]quinoline-ethanesulfonate
$ED_{500}$ = 22 s.c.
32 p.o.

6. Modified Jumping Test

This test was elaborated for screening psychoactive drugs. Setup consists of a metal plate of 45° C. and of a glass cylinder with open top and bottom. Animals placed under the glass cylinder on the plate are allowed to jump up once. Latency time between placing and jumping is registered. The time needed for escape (jumping) is taken as an index of the central nervous system (CNS) excitability and is expressed in units from 0 to 10. The tested compounds proved to be ineffective on modified jumping test.

7. Screening Test

I was elaborated for studing learning and retention of rats during one session conditioning.

During conditioning rats are trained to jump onto the top of glass cylinder by the electric foot-shock (110 V). The escape reaction (unconditioned reflex, UR) is paired with a bell as conditioned stimulus. The criterion of learning is that conditioned reflex (CR) should be elicited 10 times with 10 s intervals without reinforcement. Retention of CR is taken positive when 24 h following the experiment CR can be elicited. In these experiments animals are distributed into 4 categories on the basis of their learning ability. Learning is absent when within 20 consecutive trials unconditioned reflex (UR) does not appear; slight, when UR appears, but conditioned reflex (CR) does not; medium when CR appears following some additional pairings and excellent when CR can be elicited 10 times immediately after pairing.

The compounds of the general Formula I inhibit the development of conditional reflex in this test. In a dose of 25 mg/kg thiazolo[4,5-c]quinoline-hydrochloride and ethanesulfonate cause complete inhibition while 10 mg/kg causes strong inhibition.

Small dose of haloperidol (0.025 mg/kg) resulted in strong inhibition in developing conditioned reflex, while chlordiazepoxide in the dose of 10 mg/kg does not influence the development of CR.

8. Shuttle-box

The acquisition of a two-way conditioned avoidance reflex (CAR) was analyzed in the shuttle-box during 5 consecutive days.

The instrument was constructed by the Research Institute for Electrical Industry (Hungary). It consists of six boxes, each is separated inside by a barrier with a small gate in the middle. Animals were trained to cross the barrier under the duration of a conditioned stimulus (flash/light) and if they failed to do so they were punished with a footshock (1·3 mA, US). They were given 100 trials per day. One trial consisted of 15 s intertrial interval, followed by 15 s CS. The last 5 s of CS overlapped the first s of US. At each learning session the number of CAR and intersignal reactions (IR) was automatically counted and evaluated by multiway analysis of variance (ANOVA). The test compounds in doses of 10–25 mg/kg strongly inhibited the acquisition of conditioned reflex in the shuttle box. The number of positive responses (F) seemed to be significantly smaller comparing to controls calculated from the first experimental day.

The number of negative responses (−f) in case of 25 mg/kg was high.

The number of intersignal reactions (IR) showed slight fall. 10 and 5 mg/kg chlordiazepoxid left the acquisition of conditioned reflex and IR unchanged, however, in a dose of 10 mg/kg it increased the number of negative responses (f).

The results are summarized in Table I.

TABLE I

Effect of thiazolo[4,5-c]quinoline-ethanesulfonate (compound A) on the acquisition of conditioned reflex in a shuttle box Treatment: s.c. Reference compound: chlordiazepoxide.

| Test-compound | Dose mg/kg | 1 | 2 | 3 | 4 | 5 days |
|---|---|---|---|---|---|---|
| | | F | | | | |
| Saline | — | 25.3 | 44.8 | 54.4 | 52.9 | 55.6 |
| Compound A | 50$^x$ | 8.9 | 24.5 | 20.8 | 14.6 | 16.2 |
| | 25$^x$ | 8.1 | 25.3 | 23.3 | 30.8 | 15.5 |
| | 10 | 23.5 | 44.2 | 51.6 | 66.8 | 65.1 |

TABLE I-continued

Effect of thiazolo[4,5-c]quinoline-ethanesulfonate (compound A) on the acquisition of conditioned reflex in a shuttle box Treatment: s.c. Reference compound: chlordiazepoxide.

| Test-compound | Dose mg/kg | 1 | 2 | 3 | 4 | 5 days |
|---|---|---|---|---|---|---|
| Chlordiazepoxide | 25$^x$ | 9.7 | 12.2 | 17.9 | 20.0 | 21.4 |
| | 10 | 19.9 | 37.9 | 33.7 | 35.6 | 41.2 |
| | 5 | 23.1 | 38.7 | 35.6 | 41.1 | 50.8 |
| | | −f | | | | |
| Saline | — | 10.3 | 7.1 | 6.1 | 10.3 | 8.0 |
| Compound A | 50$^x$ | 66.8 | 35.2 | 51.5 | 61.8 | 72.8 |
| | 25$^x$ | 70.3 | 41.8 | 40.4 | 46.3 | 61.3 |
| | 10 | 17.2 | 7.1 | 2.4 | 1.2 | 6.2 |
| Chlordiazepoxide | 25$^x$ | 74.0 | 67.5 | 67.0 | 65.6 | 59.8 |
| | 10$^x$ | 32.7 | 22.8 | 31.8 | 36.5 | 40.8 |
| | 5 | 11.8 | 9.1 | 10.2 | 14.9 | 13.0 |
| | | IR | | | | |
| Saline | — | 12.2 | 15.8 | 10.2 | 9.1 | 6.4 |
| Compound A | 50$^x$ | 9.2 | 7.1 | 4.2 | 3.3 | 2.6 |
| | 25 | 11.1 | 8.8 | 7.0 | 10.3 | 4.0 |
| | 10 | 6.5 | 8.8 | 5.5 | 8.2 | 6.3 |
| Chlordiazepoxide | 25 | 6.8 | 7.3 | 6.2 | 8.2 | 6.0 |
| | 10 | 10.8 | 14.7 | 8.1 | 6.3 | 6.1 |
| | 5 | 10.8 | 14.0 | 8.9 | 6.7 | 4.2 |

$^x$significant deviation, calculated by multipoint variancy analysis (ANOVA)

9. Measurement of Motility in the Shuttle-box

The apparatus described in the shuttle-box test is used also for investigating the motility of animals. In case of motility experiment all the stimuli are switched off and the animals are allowed to move freely from one compartment of the boxes to the other. The number of the spontaneous crossings of the gate during a 30-minute observation period is avareged. Significancy is calculated by Student's t test for two means.

The compounds of the general Formula I have similar slight motility decreasing effect in this test.

10. For the Studies of Benzodiazepine (BZD) Receptor Binding crude cortical membrane preparation was used. $2/\mu M$ $^3$H-diazepam was incubated with the membrane for 1 hr at 0° C. in TRIS-citrate buffer, pH 6.8. Specific binding was determined in the presence of $10/\mu M$ diazepam. In displacement studies chlordiazepoxid was used as control drug. Chlordiazepoxid displaced $^3$H-diazepam on the receptor in concentration dependent manner, while the compounds of the general Formula I even in high concentration did not alter the specific binding of $^3$H-diazepam, thus it is not bound to the receptor.

Further details of the present invention are to be found in the following Examples without limiting the present invention to the said Examples.

EXAMPLE 1

A mixture of 17.62 g (0.1 mole) of 3-amino-4-mercapto-quinoline, 150 ml of 100% formic acid and 1.5 g of sodium pyrosulfite is refluxed for 3 hours. The reaction mixture is cooled, diluted with a mixture of 800 ml of water and 40 ml of concentrated hydrochloric acid, made alkaline to pH 10 by adding a sodium hydroxide solution and extracted three times with 200 ml of benzene each. The benzene solution is evaporated. Thus 15.0 g of thiazolo[4,5-c]quinoline are obtained, m.p.: 114°–116° C., yield 80%.

The base thus obtained is dissolved in acetone and an equivalent amount of ethane sulfonic acid is added. The thiazolo[4,5-c]quinoline-ethanesulfonate thus obtained melts at 155°–157° C.

EXAMPLE 2

One proceeds according to Example 1 except that 3-amino-7-chloro-4-mercapto-quinoline is used as starting material. The 7-chloro-thiazolo[4,5-c]quinoline thus obtained melts at 199°–200° C., yield 78%.

EXAMPLE 3

One proceeds according to Example 1 except that formic acid is replaced by trifluoro acetic acid. The 2-trifluoromethyl-thiazolo[4,5-c]quinoline thus obtained melts at 113°–114° C., yield 85%.

EXAMPLE 4

A mixture of 17.62 g (0.1 mole) of 3-amino-4-mercapto-quinoline and 500 ml of triethyl ortho formate is heated at 120°–140° C. while the alcohol formed is continuously distilled off. When the last traces of ethanol are removed, the reaction mixture is cooled, diluted with benzene and the pH is adjusted to 1 by adding ethanol containing hydrochloride acid. The precipitated crystals are filtered. Thus 21.5 g of thiazolo[4,5-c]quinoline-hydrochloride are obtained, yield 96%, m.p.: 231°–232° C.

The above hydrochloride is converted into thiazolo[4,5-c]quinoline by known methods by treatment with sodium hydroxide. M.p.: 114°–116° C.

EXAMPLE 5

The compounds enumerated in Table II are prepared in an analogous manner to Example 4 by using the corresponding starting materials:

TABLE II

| Compound | Yield % | Salt | Mp °C. |
|---|---|---|---|
| 2-Ethyl-thiazolo[4,5-c]quinoline | 85 | HCl | 208–210 |
| 2-Phenyl-thiazolo[4,5-c]quinoline | 65 | base | 157–159 |
| 7-Chloro-thiazolo[4,5-c]quinoline | 85 | base | 199–200 |
| 2-n-Propyl-thiazolo[4,5-c]quinoline | 75 | HCl | 175–177 |

EXAMPLE 6

A mixture of 17.62 g (0.1 mole) of 3-amino-4-mercapto-quinoline and 85 ml of propionic anhydride is first slowly heated to boiling and then refluxed for one hour and a half. The reaction mixture is added dropwise to 800 ml of 1% aqueous hydrochloric acid under vigorous stirring. The homogenous solution is made alkaline to pH 10 by adding sodium hydroxide solution and extracted three times with 200 ml of benzene each. The benzene solution is evaporated. Thus 19.26 g of 2-ethyl-thiazolo[4,5-c]quinoline are obtained, yield 90%, m.p.: 48°–49° C.

EXAMPLE 7

The compounds enumerated in Table III are prepared in an analogous manner to Example 6 by using the corresponding starting materials.

TABLE III

| Compound | Yield, % | M.p. °C. |
|---|---|---|
| 2-n-Propyl-thiazolo[4,5-c]quinoline | 87 | 45–51 |
| 7,8-Dimethoxy-2-methyl-thiazolo[4,5-c]quinoline | 85 | 200–202 |
| 2-Phenyl-thiazolo[4,5-c]quinoline | 80 | 157–159 |
| 7-Chloro-2-methyl-thiazolo[4,5-c]quinoline | 75 | 181–183 |

EXAMPLE 8

A mixture of 12.56 g (0.05 mole) of 3-acetamido-7-chloro-4-mercapto-quinoline and 120 g of polyphosphoric acid is heated to 140°–160° C. The reaction mixture is stirred at this temperature for 2 hours, cooled to 90° C., whereupon 700 ml of water are added under vigorous stirring. When the reaction mixture has cooled to 20° C., it is made alkaline by adding a sodium hydroxide solution. The resulting mixture comprising a precipitate is extracted three times with 150 ml of chloroform each. The chloroform layers are united and evaporated to 60 ml, whereupon 300 ml of ethanol are added. 9.3 g of 7-chloro-2-methyl-thiazolo[4,5-c]quinoline are obtained in the form of needle crystals. Yield 80%, m.p.: 181°–183° C.

EXAMPLE 9

A mixture of 17.62 g (0.1 mole) of 3-amino-4-mercapto-quinoline, 15 g (0.11 mole) of phenyl acetic acid and 200 g of polyphosphoric acid is slowly heated to 140° C. under stirring. The reaction mixture is allowed to stand at this temperature for 2 hours, cooled and added to 1000 g of crushed ice under vigorous stirring. The mixture is made alkaline with an aqueous sodium hydroxide solution, extracted three times with 250 ml of chloroform each and the chloroform extract is evaporated. Thus 16.5 g of 2-benzyl-thiazolo[4,5-c]quinoline are obtained, m.p.: 111°–113° C., yield 60%.

EXAMPLE 10

A mixture of 20.52 g (0.1 mole) of 3-amino-4-mercapto-quinoline-hydrochloride, 10.61 g (0.1 mole) of freshly distilled benzaldehyde and 200 ml of ethanol is refluxed for 2 hours, whereupon air is bubbled through the reaction mixture for several days. The precipitated crystals are filtered and recrystallized from ethanol. Thus 13.5 g of 2-phenyl-thiazolo[4,5-c]quinoline are obtained. The melting point of this product is identical with that of the compound prepared according to Example 5.

EXAMPLE 11

Tablets having the following composition are prepared:

| Component | Amount, mg/tablet |
|---|---|
| Thiazolo[4,5-c]quinoline-ethanesulfonate | 25.0 |
| Maize starch | 97.0 |
| Polyvinyl pyrrolidone | 175.0 |
| Magnesium stearate | 3.0 |
| Total weight | 300.0 |

The mixture of the active ingredient and maize starch is moistened with a 10–15% polyvinyl pyrrolidone solution, granulated and dried. The granules are thoroughly dried, admixed with the magnesium stearate and pressed to tablets.

EXAMPLE 12

Capsules having the following composition are prepared by methods of pharmaceutical industry known per se:

| Component | Amount, mg/capsule |
|---|---|
| Thiazolo[4,5-c]quinoline-hydrochloride | 20.0 |
| Lactose | 60.0 |
| Maize starch | 17.0 |
| Talc | 2.0 |
| Magnesium stearate | 1.0 |
| Total weight | 100.0 |

What we claim is:

1. A thiazolo[4,5-c] quinoline derivative of the formula I

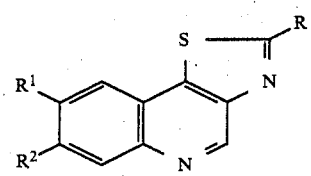

wherein

R stands for hydrogen; a straight or branched chained alkyl group having 2–5 carbon atoms optionally substituted by one or more halogen atom(s); trifluoromethyl; phenyl or phenyl-(lower alkyl) optionally bearing one or more halogen, $C_1$–$C_4$-alkyl, $C_1$–$C_4$-alkoxy, hydroxy, nitro or amino substituent(s) on the phenyl ring;

$R^1$ and $R^2$ are identical or different and stand for hydrogen, halogen or, lower alkyl or methoxy or an acid addition salt thereof.

2. Thiazolo[4,5-c]quinoline or a pharmaceutically acceptable acid addition salt thereof.

3. Thiazolo[4,5-c]quinoline-hydrochloride.

4. Thiazolo[4,5-c]quinoline-ethanesulfonate.

5. A pharmaceutical composition having major tranquilizing properties comprising: as active ingredient in a therapeutically effective amount at least one compound of the formula I as defined in claim 1 or a pharmaceutically acceptable acid addition salt thereof in admixture with a pharmaceutically acceptable carrier.

6. A pharmaceutical composition according to claim 5, wherein the active ingredient is thiazolo[4,5-c]quinoline or a pharmaceutically acceptable acid addition salt thereof.

7. A composition as described in claim 6, wherein the active ingredient is the hydrochloride or ethanesulfonate salt of thiazolo[4,5-c]quinoline.

8. A method of tranquilizing a patient in need thereof which comprises: administering to said patient an effective amount of the composition defined in claim 5.

9. A method of tranquilizing a patient in need thereof which comprises: administering to said patient an effective amount of the composition defined in claim 6.

* * * * *